(12) United States Patent
Morishige et al.

(10) Patent No.: US 9,096,842 B2
(45) Date of Patent: Aug. 4, 2015

(54) ISOPROPYL ALCOHOL-PRODUCING BACTERIUM AND METHOD FOR PRODUCING ISOPROPYL ALCOHOL

(75) Inventors: Takashi Morishige, Chiba (JP); Hitoshi Takahashi, Chiba (JP); Nozomi Takebayashi, Mobara (JP); Mitsufumi Wada, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 13/496,194

(22) PCT Filed: Sep. 13, 2010

(86) PCT No.: PCT/JP2010/065770
§ 371 (c)(1),
(2), (4) Date: Mar. 14, 2012

(87) PCT Pub. No.: WO2011/034031
PCT Pub. Date: Mar. 24, 2011

(65) Prior Publication Data
US 2012/0237992 A1    Sep. 20, 2012

(30) Foreign Application Priority Data

Sep. 16, 2009 (JP) .................... 2009-214694

(51) Int. Cl.
| | |
|---|---|
| C12N 1/20 | (2006.01) |
| C12P 7/04 | (2006.01) |
| C12N 15/00 | (2006.01) |
| C07H 21/04 | (2006.01) |
| C12N 9/88 | (2006.01) |
| C12N 9/02 | (2006.01) |
| C12N 9/10 | (2006.01) |

(52) U.S. Cl.
CPC ............... *C12N 9/88* (2013.01); *C12N 9/0008* (2013.01); *C12N 9/1029* (2013.01); *C12P 7/04* (2013.01); *C12Y 203/01016* (2013.01); *C12Y 401/01004* (2013.01)

(58) Field of Classification Search
CPC ............... C12N 15/8243; C12N 15/63; C12N 15/8246; C12N 9/88; C12N 9/14; C07K 14/245; C12Q 1/689; C12P 7/649; C12P 21/06
See application file for complete search history.

(56) References Cited

U.S. PATENT DOCUMENTS

| 2001/0049126 A1 | 12/2001 | Livshits et al. |
| 2009/0004715 A1 | 1/2009 | Trimbur et al. |
| 2010/0311135 A1* | 12/2010 | Takebayashi et al. ...... 435/157 |

FOREIGN PATENT DOCUMENTS

| EP | 1 149 911 A2 | 10/2001 |
| EP | 1 318 196 A1 | 6/2003 |
| EP | 2 184 354 A1 | 5/2010 |
| JP | 2001-346578 | 12/2001 |
| TW | 200914610 | 4/2009 |
| WO | WO-2008/151149 | 12/2008 |
| WO | WO-2009/008377 A1 | 1/2009 |
| WO | WO-2009/078687 A2 | 6/2009 |

OTHER PUBLICATIONS

Invitation to Respond to Written Opinion Singapore Patent Application No. 201201871-9 dated Jan. 14, 2013.
Jahreis, K. et al., "Adaptation of Sucrose Metabolism in the *Escherchia coli* Wild-Type Strain EC3132," J. Bacteriol., 2002, vol. 184, No. 19, pp. 5307-5316
Olson, Monica M. et al., "Production of tyrosine from sucrose or glucose achived by rapid genetic changes to phenylalanine-producing *Escherichia coli* strains," Appl. Microbiol. Biotechnol., 2007, vol. 74, pp. 1031-1040.
Sahin-Toth, M. et al., "Cloning, sequencing, and expression of cscA invertase from *Escherichia coli* B-62," Can. J. Microbiol., 1999, vol. 45, No. 5, pp. 418-422.
Search Report mailed Oct. 7, 2010 in Intl. Appln No. PCT/JP2010/065770 (2 pgs.).
Shukla, V.B., et al., "Production of D(—)-lactate from sucrose and molasses," Biotechnol. Lett., 2004, vol. 26, No. 9; pp. 689-693.
Zhou, S. et al., "Fermentation of 10% (w/v) sugar to D(—)-lactate by engineered *Escherichia coli* B," Biotechnology Letters, 2005, vol. 27, pp. 1891-1896.
Extended European Search Report dated Jan. 3, 2014 received in European Application No. 09814543.
Hanai et al., "Engineered Synthetic Pathway for Isopropanol Production in *Escherichia coli*," Applied and Environmental Microbiology, vol. 73, No. 24, 2007, pp. 7814-7818.
Japanese Office Action dated Oct. 8, 2013 issued in corresponding Japanese Patent Application No. 2011-531922, with English translation.
Jojima et al., "Production of isopropanol by metabolically engineered *Escherichia coli*," Appl Microbiol Biotechnol, vol. 77, 2008, pp. 1219-1224.
Office Action issued in Taiwan Patent Application dated Feb. 25, 2015.

* cited by examiner

*Primary Examiner* — Iqbal H Chowdhury
(74) *Attorney, Agent, or Firm* — Foley & Lardner LLP (57) ABSTRACT

The present invention provides an isopropyl alcohol-producing *Escherichia coli* that includes at least a sucrose hydrolase gene that belongs to a sucrose non-PTS gene group, and an imparted or enhanced isopropyl alcohol production system, and an isopropyl alcohol production method of producing isopropyl alcohol from a sucrose-containing plant-derived raw material using the isopropyl alcohol-producing *Escherichia coli*.

9 Claims, 1 Drawing Sheet

SEQUENCE LISTING

```
<160> NUMBER OF SEQ ID NOS: 26

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
cgagctacat atgcaatgat tgacacgatt ccg                          33

<210> SEQ ID NO 2
<211> LENGTH: 32
<212> TYPE: DNA
<213> ORGANISM: Artificial
<220> FEATURE:
<223> OTHER INFORMATION: primer

<400> SEQUENCE: 2
cgcgcgcatg ctatttgtta gtgaataaaa gg                           32

<210> SEQ ID NO 3
<211> LENGTH: 45
<212> TYPE: DNA
<213> ORGANISM: Artificial
<220> FEATURE:
<223> OTHER INFORMATION: primer

<400> SEQUENCE: 3
aatatgcatg ctggtggaac atatgaaagg ttttgcaatg ctagg             45

<210> SEQ ID NO 4
<211> LENGTH: 44
<212> TYPE: DNA
<213> ORGANISM: Artificial
<220> FEATURE:
<223> OTHER INFORMATION: primer

<400> SEQUENCE: 4
```

```
gcggatccgg taccttataa tataactact gctttaatta agtc            44
```

<210> SEQ ID NO 5
<211> LENGTH: 44
<212> TYPE: DNA
<213> ORGANISM: Artificial
<220> FEATURE:
<223> OTHER INFORMATION: primer

<400> SEQUENCE: 5

```
atggatccgc tggtggaaca tatgaaaaat tgtgtcatcg tcag            44
```

<210> SEQ ID NO 6
<211> LENGTH: 42
<212> TYPE: DNA
<213> ORGANISM: Artificial
<220> FEATURE:
<223> OTHER INFORMATION: primer

<400> SEQUENCE: 6

```
gcagaagctt gtctagatta attcaaccgt tcaatcacca tc              42
```

<210> SEQ ID NO 7
<211> LENGTH: 51
<212> TYPE: DNA
<213> ORGANISM: Artificial
<220> FEATURE:
<223> OTHER INFORMATION: primer

<400> SEQUENCE: 7

```
gctctagagc tggtggaaca tatgaaaaca aaattgatga cattacaaga c    51
```

<210> SEQ ID NO 8
<211> LENGTH: 41
<212> TYPE: DNA
<213> ORGANISM: Artificial
<220> FEATURE:
<223> OTHER INFORMATION: primer

<400> SEQUENCE: 8

```
tagcaagctt ctactcgagt tatttgctct cctgtgaaac g               41
```

<210> SEQ ID NO 9
<211> LENGTH: 44
<212> TYPE: DNA
<213> ORGANISM: Artificial
<220> FEATURE:
<223> OTHER INFORMATION: primer

<400> SEQUENCE: 9

```
aagtctcgag ctggtggaac atatggatgc gaaacaacgt attg            44
```

<210> SEQ ID NO 10
<211> LENGTH: 28
<212> TYPE: DNA
<213> ORGANISM: Artificial
<220> FEATURE:
<223> OTHER INFORMATION: primer

<400> SEQUENCE: 10

```
ggccaagctt cataaatcac cccgttgc                              28
```

<210> SEQ ID NO 11
<211> LENGTH: 35
<212> TYPE: DNA

<213> ORGANISM: Artificial
<220> FEATURE:
<223> OTHER INFORMATION: primer

<400> SEQUENCE: 11
gctggtggaa catatgacgc aatctcgatt gcatg					35

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
ttaacccagt tgccagagtg c					21

<210> SEQ ID NO 13
<211> LENGTH: 54
<212> TYPE: DNA
<213> ORGANISM: Artificial
<220> FEATURE:
<223> OTHER INFORMATION: primer

<400> SEQUENCE: 13
caggtaccgc tggtggaaca tatgttaaag gatgaagtaa ttaaacaaat tagc					54

<210> SEQ ID NO 14
<211> LENGTH: 38
<212> TYPE: DNA
<213> ORGANISM: Artificial
<220> FEATURE:
<223> OTHER INFORMATION: primer

<400> SEQUENCE: 14
gcggatcctt acttaagata atcatatata acttcagc					38

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
cgctcaattg caatgattga cacgattccg					30

<210> SEQ ID NO 16
<211> LENGTH: 32
<212> TYPE: DNA
<213> ORGANISM: Artificial
<220> FEATURE:
<223> OTHER INFORMATION: primer

<400> SEQUENCE: 16
acagaattcg ctatttgtta gtgaataaaa gg					32

<210> SEQ ID NO 17
<211> LENGTH: 50
<212> TYPE: DNA
<213> ORGANISM: Artificial
<220> FEATURE:
<223> OTHER INFORMATION: primer

<400> SEQUENCE: 17
cgaattcgct ggtggaacat atgaaaacaa aattgatgac attacaagac					50

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
gcggtacctt atttgctctc ctgtgaaacg                                   30

<210> SEQ ID NO 19
<211> LENGTH: 31
<212> TYPE: DNA
<213> ORGANISM: Artificial
<220> FEATURE:
<223> OTHER INFORMATION: primer

<400> SEQUENCE: 19
gctctagatg ctgaaatcca ctagtcttgt c                                 31

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
tactgcagcg ttccagcacc ttatcaacc                                    29

<210> SEQ ID NO 21
<211> LENGTH: 29
<212> TYPE: DNA
<213> ORGANISM: Artificial
<220> FEATURE:
<223> OTHER INFORMATION: primer

<400> SEQUENCE: 21
ggtctagagc aatgattgac acgattccg                                    29

<210> SEQ ID NO 22
<211> LENGTH: 38
<212> TYPE: DNA
<213> ORGANISM: Artificial
<220> FEATURE:
<223> OTHER INFORMATION: primer

<400> SEQUENCE: 22
gcggatcctt ataatataac tactgcttta attaagtc                          38

<210> SEQ ID NO 23
<211> LENGTH: 54
<212> TYPE: DNA
<213> ORGANISM: Artificial
<220> FEATURE:
<223> OTHER INFORMATION: primer

<400> SEQUENCE: 23
caggatccgc tggtggaaca tatgttaaag gatgaagtaa ttaaacaaat tagc         54

<210> SEQ ID NO 24
<211> LENGTH: 43
<212> TYPE: DNA
<213> ORGANISM: Artificial Sequence
<220> FEATURE:

```
<223> OTHER INFORMATION: primer
<220> FEATURE:
<221> NAME/KEY: primer
<222> LOCATION: (1)..(24)
<223> OTHER INFORMATION:

<400> SEQUENCE: 24
ggaattcggt accttactta agataatcat atataacttc agc                    43

<210> SEQ ID NO 25
<211> LENGTH: 43
<212> TYPE: DNA
<213> ORGANISM: Artificial
<220> FEATURE:
<223> OTHER INFORMATION: primer

<400> SEQUENCE: 25
atggtaccgc tggtggaaca tatgacgcaa tctcgattgc atg                    43

<210> SEQ ID NO 26
<211> LENGTH: 28
<212> TYPE: DNA
<213> ORGANISM: Artificial
<220> FEATURE:
<223> OTHER INFORMATION: primer

<400> SEQUENCE: 26
cgaattctta acccagttgc cagagtgc                                     28
```

ISOPROPYL ALCOHOL-PRODUCING BACTERIUM AND METHOD FOR PRODUCING ISOPROPYL ALCOHOL

TECHNICAL FIELD

The present invention relates to an isopropyl alcohol-producing bacterium and a method for producing isopropyl alcohol.

BACKGROUND ART

Propylene is an important basic raw material for synthetic resins such as polypropylene and for petrochemical products, and is used widely such as for automobile bumpers, food containers, films, and medical instruments.

Isopropyl alcohol produced from plant-derived raw materials can be converted to propylene through a dehydration process. Therefore, isopropyl alcohol is a promising carbon-neutral raw material for propylene. Kyoto Protocol called for industrialized nations to reduce their total carbon dioxide emissions from 1990 levels by 5 percent by 2008-2012. Therefore, carbon-neutral propylene is currently extremely important due to its versatility, in view of the global environment.

Bacteria that assimilate plant-derived raw materials and produce isopropyl alcohol are already known. For example, WO 2009/008377 discloses a bacterium that has been modified so as to achieve high production of isopropyl alcohol from glucose as a raw material, and describes that the bacterium is an excellent biocatalyst for industrial production of isopropyl alcohol.

It is known that *Escherichia coli* cannot assimilate sucrose. However, it would be industrially advantageous if sucrose, which is inexpensive among plant-derived materials, could be utilized.

According to conventional knowledge, the mechanism of sucrose assimilation by microorganisms is roughly classified into two systems, i.e., the sucrose PTS (Phosphoenolpyruvate: Carbohydrate Phosphotransferase System) and the sucrose non-PTS (For example, JP-A No. 2001-346578). The sucrose non-PTS is known to be composed of four factors, i.e., cscB (which incorporates sucrose), cscA (which decomposes sucrose in microorganisms), cscK (which phosphorylates fructose), and cscR (which controls the expressions of cscB, A, and K). Biotechnology Letters, Vol. 27, pp. 1891-1896 (2005) describes that genes of these four factors were introduced into D-lactic acid-producing *Escherichia coli* using plasmids, thereby producing D-lactic acid from sucrose.

In addition, the sucrose PTS is known to be composed of five factors, i.e., scrA (which incorporates sucrose); scrY (which phosphorylates sucrose); scrB (which decomposes sucrose in microorganisms); scrR (which controls the expressions of scrA, Y, and B), and scrK (which phosphorylates fructose).

When ability that a microorganism does not have should be introduced into the microorganism, introduction of a gene expressing the ability is generally studied. In the case of sucrose assimilation ability, the DNAs of the above factors have sizes of from 900 to 1500 bp, and the total DNA size required for expressing genes of four enzymes (thiolase, CoA transferase, acetoacetate decarboxylase, and isopropyl alcohol dehydrogenase) required for high production of isopropyl alcohol is approximately 4800 bp. In other words, introduction of a DNA having a size of approximately 9300 bp would be necessary in order to impart both the sucrose assimilation ability and the IPA-producing ability to *Escherichia coli*.

However, simultaneous introduction thereof into *Escherichia coli* is extremely difficult since the size of the DNA to be introduced would exceed the upper limit of the DNA size which the plasmid can accommodate. Even if two kinds of plasmid vector were used so as to reduce the DNA size of each plasmid to be 10000 bp or smaller, either or both of the two kinds of plasmid introduced into *Escherichia coli* would usually be likely to be eliminated during repetitive growth. The *Escherichia coli* would need to be continuously exposed to an expensive antibiotic substance as a selection marker in order to avoid the above problem, and such necessity is not suitable for industrial production.

Accordingly, it was difficult to simultaneously impart both the ability to assimilate sucrose and the ability to highly produce isopropyl alcohol to *Escherichia coli*.

Can. J. Microbiol., Vol. 45, pp. 18-422 (1999) discloses that as a result of introduction of sucrose hydrolase (cscA) alone into *Escherichia coli*, the *Escherichia coli* could grow using sucrose as a raw material. However, the article also demonstrates that when cscA gene was highly expressed by a genetic recombination technology, almost all of cscA were present in the cells. Thus, cscA (invertase) works inside the cells rather than outside the cells, and it cannot be expected that cscA decomposes sucrose outside the cells.

An example of material production from sucrose using *Escherichia coli*, which cannot assimilate sucrose, is production of tryptophan using sucrose as a raw material (for example, JP-A No. 2001-346578). However, in this example, it is demonstrated that introduction of a group of genes including at least cscA, cscB, and cscK is necessary in order to impart the ability to produce amino acids from sucrose to *Escherichia coli*.

SUMMARY OF INVENTION

Technical Problem to be Solved by Invention

As discussed above, it has been extremely difficult to simultaneously impart the ability to assimilate sucrose and the ability to highly produce isopropyl alcohol to *Escherichia coli*, which cannot assimilate sucrose, due to the excessively large size of the DNA to be introduced.

An object of the present invention is to provide an isopropyl alcohol-producing *Escherichia coli* and a method for producing isopropyl alcohol that are useful for efficient production of isopropyl alcohol from sucrose, which is inexpensive and has high industrial utility value.

The present invention provides an isopropyl alcohol-producing *Escherichia coli* and a method for producing isopropyl alcohol as described below.

Means for Solving Problem

[1] An isopropyl alcohol-producing *Escherichia coli* including at least a sucrose hydrolase gene that belongs to a sucrose non-PTS gene group, and an imparted or enhanced isopropyl alcohol production system.

[2] The isopropyl alcohol-producing *Escherichia coli* according to [1], including only the sucrose hydrolase gene from among genes belonging to the sucrose non-PTS gene group.

[3] The isopropyl alcohol-producing *Escherichia coli* according to [1] or [2], wherein the isopropyl alcohol-producing *Escherichia coli* is an *Escherichia coli* to which an acetoacetate decarboxylase activity, an isopropyl alcohol dehydrogenase activity, a CoA transferase activity, and a thiolase activity have been imparted.

[4] The isopropyl alcohol-producing *Escherichia coli* according to [3], wherein the acetoacetate decarboxylase activity, the isopropyl alcohol dehydrogenase activity, the CoA transferase activity, and the thiolase activity are obtained by introduction of genes encoding respective enzymes which are derived from at least one selected from the group consisting of bacteria of the genus *Clostridium*, bacteria of the genus *Bacillus*, and bacteria of the genus *Escherichia*.

[5] The isopropyl alcohol-producing *Escherichia coli* according to [3], wherein the acetoacetate decarboxylase activity and the isopropyl alcohol dehydrogenase activity are obtained by introduction of genes encoding respective enzymes which are derived from a bacterium or bacteria of the genus *Clostridium*, and the CoA transferase activity and the thiolase activity are obtained by introduction of genes encoding respective enzymes which are derived from a bacterium or bacteria of the genus *Escherichia*.

[6] The isopropyl alcohol-producing *Escherichia coli* according to [3], wherein the acetoacetate decarboxylase activity is obtained by introduction of a gene encoding an enzyme derived from *Clostridium acetobutylicum*, the isopropyl alcohol dehydrogenase activity is obtained by introduction of a gene encoding an enzyme derived from *Clostridium beijerinckii*, and the CoA transferase activity and the thiolase activity are obtained by introduction of genes encoding respective enzymes derived from *Escherichia coli*.

[7] The isopropyl alcohol-producing *Escherichia coli* according to [3], wherein a gene encoding the acetoacetate decarboxylase, a gene encoding the isopropyl alcohol dehydrogenase, and the gene encoding the sucrose hydrolase have been introduced using at least one plasmid, and the CoA transferase activity and the thiolase activity are obtained from genomic genes in the host *Escherichia coli*.

[8] The isopropyl alcohol-producing *Escherichia coli* according to [7], wherein a promoter for expressing a gene encoding the CoA transferase and a gene encoding the thiolase is at least one of a glyceraldehyde-3-phosphate dehydrogenase promoter or a serine hydroxymethyltransferase promoter.

[9] The isopropyl alcohol-producing *Escherichia coli* according to [3], wherein the acetoacetate decarboxylase activity, the isopropyl alcohol dehydrogenase activity, the CoA transferase activity and the thiolase activity are all obtained by introduction of genes encoding respective enzymes derived from a bacterium or bacteria of the genus *Clostridium*.

[10] A method for producing isopropyl alcohol, including producing isopropyl alcohol from a sucrose-containing plant-derived raw material using the isopropyl alcohol-producing *Escherichia coli* according to any one of [1] to [9].

DESCRIPTION OF EMBODIMENTS

An isopropyl alcohol-producing *Escherichia coli* according to the present invention is an isopropyl alcohol-producing *Escherichia coli* which includes at least a sucrose hydrolase gene belonging to the sucrose non-PTS gene group, and an imparted or enhanced isopropyl alcohol production system.

A method for producing isopropyl alcohol according to the present invention is an isopropyl alcohol production method that includes producing isopropyl alcohol from a sucrose-containing plant-derived raw material using the above-described isopropyl alcohol-producing *Escherichia coli*.

The isopropyl alcohol-producing *Escherichia coli* according to the present invention includes at least a sucrose hydrolase gene that is a member of the sucrose non-PTS gene group in order to assimilate sucrose, and also has an isopropyl alcohol production system. Thus, the *Escherichia coli*, which lacks innate ability to assimilate sucrose, simultaneously exerts the ability to assimilate sucrose and the ability to produce isopropyl alcohol, so that isopropyl alcohol can be efficiently produced from sucrose. So far, there has been no report on a case in which the sucrose non-PTS gene group is introduced into *Escherichia coli*, which lacks the sucrose assimilation ability, to produce isopropyl alcohol using sucrose as a carbon source.

The present invention has found that, as a result of introduction of at least a sucrose hydrolase gene which is a member of the group of genes constituting the non-PTS gene group into an isopropyl alcohol-producing *Escherichia coli*, sucrose can be assimilated with high efficiency in the *Escherichia coli* which highly produces isopropyl alcohol. As a result of this, the size of the DNA to be introduced for imparting the sucrose assimilation ability can be remarkably reduced, whereby it is made possible to simultaneously connect a DNA for imparting the sucrose assimilation ability and a DNA for imparting an isopropyl alcohol production ability to a single plasmid vector. Thereby, the sucrose assimilation ability and the isopropyl alcohol-production ability can be simultaneously imparted to *Escherichia coli*, which cannot assimilate sucrose, so that isopropyl alcohol can be efficiently obtained from inexpensive sucrose derived from sugarcane or sugar beet, which can be supplied in large amounts.

In particular, the isopropyl alcohol-producing *Escherichia coli* according to the present invention is able to assimilate glucose and fructose—decomposition products of sucrose—almost simultaneously, and to produce isopropyl alcohol. Therefore the *Escherichia coli* according to the invention has higher efficiency.

In general, in *Escherichia coli*, it is known that the uptake of glucose usually has priority over the uptake of fructose, and fructose is not sufficiently metabolized in the presence of glucose. Accordingly, it is surprising that isopropyl alcohol could be efficiently produced without being affected by catabolite repression by glucose.

In the present invention, the term "host" means *Escherichia coli* that will become the isopropyl alcohol-producing *Escherichia coli* according to the present invention as a result of the introduction of one or more genes from outside the cell thereof.

The scope of the term "process" as used herein includes not only a discrete process, but also a process that cannot be clearly distinguished from another process as long as the expected effect of the process of interest is achieved.

In addition, any numerical range expressed herein using "to" include the numerical values before and after "to" as the minimum and maximum values, respectively.

In the following, the present invention is described.

The sucrose non-PTS gene group in the present invention refers to a group of four genes involved in the non-PTS system among sucrose assimilation pathways of a microorganism. Specifically, sucrose non-PTS gene group is a gene group composed of a repressor protein (cscR), a sucrose hydrolase (cscA), a fructokinase (cscK), and a sucrose permease (cscB). In the present invention, at least one thereof, including at least cscA, may be used. For example, cscA only, a combination of cscA and cscK, a combination of cscA and cscB, a combination of cscA and cscR, a combination of cscA, cscR, and cscK, or a combination of cscA, cscR, and cscB, may be used. In particular, from the viewpoint of more efficiently producing isopropyl alcohol, it is preferable that only a gene encoding cscA is included while the other genes of the sucrose non-PTS gene group are not included.

The sucrose hydrolase (invertase, CscA) in the present invention refers to a generic name of enzymes which are classified as enzyme code number: 3.2.1.26 based on the report of the Enzyme Commission of the International Union of Biochemistry (I.U.B), and which catalyze a reaction of producing D-glucose and D-fructose from sucrose.

This enzyme is an enzyme that *Escherichia coli* such as K12 strain and B strain does not naturally possess, and is one of the enzymes of the non-PTS metabolic pathways including a proton symporter, an invertase, a fructokinase, and a sucrose-specific repressor (see Canadian Journal of Microbiology, (1991) vol. 45, pp 418-422). In the present invention, as a result of imparting CscA, particularly as a result of imparting cscA only, extracellular sucrose is decomposed into glucose and fructose on the cell membrane, and the glucose and fructose are released to outside the cell, and phosphorylated and incorporated into the cytoplasm via a glucose PTS and a fructose PTS. As a result, fructose is supplied to a fructose metabolic system in the bacterium to allow for assimilation using a glycolytic system.

As a gene of the sucrose hydrolase (invertase, CscA) to be introduced into the host bacterium in the present invention, a DNA having the base sequence of a gene encoding the sucrose hydrolase (invertase, CscA) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of the gene derived from an *Escherichia coli* O157 strain. Particularly preferred is a DNA having the base sequence of the gene derived from an *Escherichia coli* O157 strain. It is preferable that a signal sequence for transferring cscA to the periplasm of the bacterial cell has been added to cscA.

As a gene of the repressor protein (CscR) to be introduced into the host bacterium in the present invention, a DNA having the base sequence of a gene encoding the repressor protein (CscR) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of the gene derived from an *Escherichia coli* O157 strain. The DNA having the base sequence of the gene derived from an *Escherichia coli* O157 strain is particularly preferable.

As a gene of the fructokinase (CscK) to be introduced into the host bacterium in the present invention, a DNA having the base sequence of a gene encoding the fructokinase (CscK) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of the gene derived from an *Escherichia coli* O157 strain. The DNA having the base sequence of the gene derived from an *Escherichia coli* O157 strain is particularly preferable.

As a gene of the sucrose permease (CscB) to be introduced into the host bacterium in the present invention, a DNA having the base sequence of a gene encoding the sucrose permcase (CscB) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of the gene derived from an *Escherichia coli* O157 strain. The DNA having the base sequence of the gene derived from an *Escherichia coli* O157 strain is particularly preferable.

The isopropyl alcohol-producing *Escherichia coli* in the present invention refers to *Escherichia coli* that possesses the ability to produce isopropyl alcohol which has been introduced or modified by genetic recombination. Due to the isopropyl alcohol-producing *Escherichia coli* possessing the introduced or modified isopropyl alcohol production ability in combination with the CscA activity mentioned above, even *Escherichia coli*, which does not have innate sucrose assimilation ability, becomes to be able to effectively produce isopropyl alcohol from sucrose.

The scope of the phrase "by genetic recombination" as used in the present invention includes any change in a base sequence caused by insertion of another DNA into the base sequence of a native gene, or by substitution or deletion of a specific region of a gene, or by any combination thereof. For example, the genetic recombination may result from mutation.

In the present invention, the sucrose assimilation refers to the ability to incorporate into a living organism, sucrose as it is or by converting sucrose to a substance having a higher or lower molecular weight, preferably to a substance having a lower molecular weight, or refers to the ability to metabolically convert sucrose into another substance. The scope of assimilation as used in the present invention includes decomposition by which sucrose is converted to a substance having a lower molecular weight, and specifically includes decomposition of sucrose into D-glucose and D-fructose.

The isopropyl alcohol-producing system in the present invention may be any system that allows target *Escherichia coli* to produce isopropyl alcohol.

In the present invention, the imparted or enhanced isopropyl alcohol production system refers to a structure for demonstrating the isopropyl alcohol production ability that has been introduced or modified by genetic recombination. The isopropyl alcohol production system may be any isopropyl alcohol production system that increases isopropyl alcohol production of target *Escherichia coli* as compared to its original isopropyl alcohol production. Preferable examples include inactivation, reduction, or enhancement of enzyme activity involved with isopropyl alcohol production activity, or a combination thereof. Due to the isopropyl alcohol production system in combination with the CscA activity mentioned above, even *Escherichia coli*, which does not have innate sucrose assimilation ability, becomes to be able to effectively produce isopropyl alcohol from sucrose.

A preferable example is provision of enhanced enzyme activity involved with the production of isopropyl alcohol. A more preferable example is enhancement of the enzyme activity of thiolase, CoA transferase, acetoacetate decarboxylase, and isopropyl alcohol dehydrogenase. In other words, four kinds of enzyme activity, i.e., acetoacetate decarboxylase activity, isopropyl alcohol dehydrogenase activity, CoA transferase activity, and thiolase activity are preferably imparted to the isopropyl alcohol-producing *Escherichia coli* according to the present invention.

In the present invention, the scope of the "impartment" of activity includes introduction of an enzyme-encoding gene from outside of the bacterial cell of the host bacterium into the inside of the bacterial cell, and further includes high expression of an enzyme gene by enhancement of the promoter activity of an enzyme gene that the host bacterium possesses on the genome thereof or by substitution with another promoter, In the present invention, the acetoacetate decarboxylase refers to a generic name of enzymes which are classified as enzyme code number: 4.1.1.4 based on the report of the Enzyme Commission of the International Union of Biochemistry (I.U.B), and which catalyze a reaction of producing acetone from acetoacetate.

Examples of the enzymes include those derived from bacteria of the genus *Clostridium*, such as *Clostridium acetobutylicum* and *Clostridium beijerinckii*, and bacteria of the genus *Bacillus* such as *Bacillus polymyxa*.

As a gene of the acetoacetate decarboxylase to be introduced into the host bacterium of the present invention, a DNA having the base sequence of a gene encoding the acetoacetate decarboxylase obtained from any of the above-listed enzyme origin organisms, or a synthetic DNA sequence that is synthesized based on a known base sequence of the gene, may be used. Preferable examples include those derived from bacteria of the genus *Clostridium* or bacteria of the genus *Bacillus*. An example is a DNA having the base sequence of the gene derived from *Clostridium acetobutylicum* or *Bacillus polymyxa*. A DNA having the base sequence of the gene derived from *Clostridium acetobutylicum* is particularly preferable.

In the present invention, the isopropyl alcohol dehydrogenase refers to a generic name of enzymes which are classified as enzyme code number: 1.1.1.80 based on the report of the Enzyme Commission of the International Union of Biochemistry (I.U.B), and which catalyze a reaction of producing isopropyl alcohol from acetone. Examples of the enzyme include those derived from bacteria of the genus *Clostridium*, such as *Clostridium beijerinckii*.

As a gene of the isopropyl alcohol dehydrogenase to be introduced into the host bacterium of the present invention, a DNA having the base sequence of a gene encoding the isopropyl alcohol dehydrogenase obtained from any of the above-listed enzyme origin organisms, or a synthetic DNA sequence that is synthesized based on a known base sequence of the gene, may be used. Preferable examples include those derived from bacteria of the genus *Clostridium*, such as a DNA having the base sequence of the gene derived from *Clostridium beijerinckii*.

In the present invention, the CoA transferase refers to a generic name of enzymes which are classified as enzyme code number: 2.8.3.8 based on the report of the Enzyme Commission of the International Union of Biochemistry (I.U.B), and which catalyze a reaction of producing acetoacetate from acetoacetyl CoA.

Examples of the enzyme include those derived from bacteria of the genus *Clostridium*, such as *Clostridium acetobutylicum* and *Clostridium beijerinckii*, bacteria of the genus *Roseburia*, such as *Roseburia intestinalis*, bacteria of the genus *Faecalibacterium* such as *Faecalibacterium prausnitzii*, bacteria of the genus *Coprococcus*, bacteria of the genus *Trypanosoma* such as *Trypanosoma brucei*, and bacteria of the genus *Escherichia* such as *Escherichia coli*.

As a gene of the CoA transferase to be introduced into the host bacterium of the present invention, a DNA having the base sequence of a gene encoding the CoA transferase obtained from any of the above-listed enzyme origin organisms, or a synthetic DNA sequence that is synthesized based on a known base sequence of the gene, may be used. Preferable examples include a DNA having the base sequence of the gene derived from a bacterium of the genus *Clostridium* such as *Clostridium acetobutylicum*, a bacterium of the genus *Roseburia* such as *Roseburia intestinalis*, a bacterium of the genus *Faecalibacterium* such as *Faecalibacterium prausnitzii*, a bacterium of the genus *Coprococcus*, a bacterium of the genus *Trypanosoma* such as *Trypanosoma brucei*, or a bacterium of the genus *Escherichia* such as *Escherichia coli*. A DNA having the base sequence of the gene derived from a bacterium of the genus *Clostridium* or a bacterium of the genus *Escherichia* is more preferable, and a DNA having the base sequence of the gene derived from *Clostridium acetobutylicum* or *Escherichia coli* is particularly preferable.

In the present invention, the thiolase refers to a generic name of enzymes which are classified as enzyme code number: 2.3.1.9 based on the report of the Enzyme Commission of the International Union of Biochemistry (I.U.B), and which catalyze a reaction of producing acetoacetyl CoA from acetyl CoA.

Examples of the enzyme include those derived from bacteria of the genus *Clostridium* such as *Clostridium acetobutylicum* and *Clostridium beijerinckii*, bacteria of the genus *Escherichia* such as *Escherichia coli*, bacteria of the species *Halobacterium*, bacteria of the genus *Zoogloea* such as *Zoogloea ramigera*, bacteria of the species *Rhizobium*, bacteria of the genus of *Bradyrhizobium* such as *Bradyrhizobium japonicum*, bacteria of the genus *Candida* such as *Candida tropicalis*, bacteria of the genus *Caulobacter* such as *Caulobacter crescentus*, bacteria of the genus *Streptomyces* such as *Streptomyces collinus*, and bacteria of the genus *Enterococcus* such as *Enterococcus faecalis*.

As a gene of the thiolase to be introduced into the host bacterium of the present invention, a DNA having the base sequence of a gene encoding the thiolase obtained from any of the above-listed enzyme origin organisms, or a synthesized DNA sequence that is synthesized based on a known base sequence of the gene, may be used. Preferable examples include a DNA having the base sequence of the gene derived from a bacterium of the genus *Clostridium* such as *Clostridium acetobutylicum* or *Clostridium beijerinckii*, a bacterium of the genus *Escherichia* such as *Escherichia coli*, a bacterium of the species *Halobacterium*, a bacterium of the genus *Zoogloea* such as *Zoogloea ramigera*, a bacterium of the species *Rhizobium*, a bacterium of the genus *Bradyrhizobium* such as *Bradyrhizobium japonicum*, a bacterium of the genus *Candida* such as *Candida tropicalis*, a bacterium of the genus *Caulobacter* such as *Caulobacter crescentus*, a bacterium of the genus *Streptomyces* such as *Streptomyces collinus*, or a bacterium of the genus *Enterococcus* such as *Enterococcus faecalis*. A DNA having the base sequence of the gene derived from a bacterium of the genus *Clostridium* or a bacterium of the genus *Escherichia* is more preferable, and a DNA having the base sequence of the gene derived from *Clostridium acetobutylicum* or *Escherichia coli* is particularly preferable.

Among them, from the viewpoint of enzyme activity, it is preferable that each of the four kinds of enzyme is an enzyme derived from at least one selected from the group consisting of a bacterium of the genus *Clostridium*, a bacterium of the genus *Bacillus*, and a bacterium of the genus *Escherichia*. In particular, a case in which the acetoacetate decarboxylase and the isopropyl alcohol dehydrogenase are derived from a bacterium or bacteria of the genus *Clostridium*, and the CoA transferase activity and the thiolase activity are derived from a bacterium or bacteria of the genus *Escherichia*, and a case in which the four kinds of enzyme are all derived from a bacterium or bacteria of the genus *Clostridium*, are more preferable.

In particular, from the viewpoint of the enzyme activity, it is preferable that each of the four kinds of enzyme in the present invention is derived from any of *Clostridium acetobutylicum, Clostridium beijerinckii*, or *Escherichia coli*. More preferably, the acetoacetate decarboxylase is an enzyme derived from *Clostridium acetobutylicum*, each of the CoA transferase and the thiolase is an enzyme derived from *Clostridium acetobutylicum* or *Escherichia coli*, and the isopropyl alcohol dehydrogenase is an enzyme derived from *Clostridium beijerinckii*. In regard to the four kinds of enzyme, particularly preferably, the acetoacetate decarboxylase activity is derived from *Clostridium acetobutylicum*, the isopropyl alcohol dehydrogenase activity is derived from *Clostridium beijerinckii*, and the CoA transferase activity and the thiolase activity are derived from *Escherichia coli*, from the viewpoint of the enzyme activity.

When the CoA transferase activity and the thiolase activity are derived from *Escherichia coli*, preferably, the gene encoding the acetoacetate decarboxylase, the gene encoding the isopropyl alcohol dehydrogenase and the gene encoding the sucrose hydrolase are introduced by at least one plasmid, and the CoA transferase activity and the thiolase activity are obtained from genomic genes in the host *Escherichia coli*, from the viewpoint of the isopropyl alcohol production ability.

In the present invention, an example of *Escherichia coli* of which the enzyme activity involved with the production of isopropyl alcohol is enhanced to produce isopropyl alcohol is the pIPA/B strain or the pIaaa/B strain described in WO 2009/008377.

The gene promoter in the invention may be any promoter that is capable of controlling the expression of a gene from among the above genes. The gene promoter may be a powerful promoter which constitutively works in the microorganism, and which is not susceptible to repression of expression even in the presence of glucose. Specific examples thereof include the promoter of glyceraldehyde-3-phosphate dehydrogenase (hereinafter also referred to as GAPDH) or the promoter of serine hydroxymethyltransferase.

The promoter in the present invention means a region to which an RNA polymerase having a sigma factor hinds to start transcription. For example, a GAPDH promoter derived from *Escherichia coli* is described at Base Nos. 397-440 in the base sequence information of GenBank accession number X02662.

CoA transferase genes (atoD and atoA) and a thiolase gene (atoB), each of which is derived from *Escherichia coli*, form an operon on the genome of *Escherichia coli* in the order of atoD, atoA, and atoB (Journal of Baceteriology Vol. 169 pp 42-52 Lauren Sallus Jenkins, at al.) Therefore, the expressions of the CoA transferase genes and the thiolase gene can be simultaneously controlled by modifying the promoter of atoD.

In view of the above, when the CoA transferase activity and the thiolase activity are obtained from the genomic genes of the host *Escherichia coli*, it is preferable to enhance the expression of both enzyme genes by, for example, replacing the promoter responsible for the expression of both enzyme genes by another promoter, from the viewpoint of obtaining sufficient isopropyl alcohol production ability. Examples of the promoter to be used in order to enhance the CoA transferase activity and the thiolase activity include the above-described *Escherichia coli*-derived GAPDH promoter.

The activity of those enzymes in the present invention may be provided by introducing the enzymatic activity from the outside of the bacterial cell into the inside of the bacterial cell, or by high expression of the enzyme genes that the host bacterium has on its genome by enhancement of the promoter activity of the enzyme genes or substitution with another promoter.

The introduction of the enzyme activity can be carried out by, for example, introducing the genes encoding the four kinds of enzyme from the outside of the bacterial cell of the host bacterium into the inside of the bacterial cell using a genetic recombination technique. Here, the enzyme genes to be introduced may be conspecific or heterospecific to the host cell. Methods for the preparation of the genomic DNA necessary for the gene introduction from the outside of the bacterial cell into the inside of the cell, the cleavage and ligation of DNAs, transformation, PCR (Polymerase Chain Reaction), the design and synthesis of the oligonucleotides used as primers, and the like, can be carried out by ordinary methods well-known to those skilled in the art. Those methods are described in, for example, Sambrook, J., et. al., "Molecular Cloning A laboratory Manual, Second Edition", Cold Spring Harbor Laboratory Press, (1989).

The scope of the "impartment" or "enhancement" of ability as used in the present invention includes introduction of an enzyme-encoding gene from outside of the bacterial cell of the host bacterium into the inside of the bacterial cell, and further includes high expression of an enzyme gene by enhancement of the promoter activity of an enzyme gene that the host bacterium possesses on the genome thereof or by substitution with another promoter.

In the present invention, the *Escherichia coli* to which enzyme activity has been imparted refers to *Escherichia coli* to which the enzyme activity has been imparted from the outside of the bacterial cell to the inside of the bacterial cell using a certain method. Such *Escherichia coli* can be produced using a method of, for example, introducing a gene encoding the enzyme and protein from the outside of the bacterial cell into the inside of the bacterial cell using the genetic recombination technique as described above.

In the present invention, *Escherichia coli* of which the enzyme activity is enhanced refers to *Escherichia coli* of which the enzyme activity is enhanced by a certain method. Such *Escherichia coli* can be produced using a method of, for example, introducing a gene encoding the enzyme and protein from the outside of the bacterial cell into the inside of the bacterial cell by using a plasmid and using the genetic recombination technique as the described above, or causing high expressions of an enzyme gene that the host *Escherichia coli* possesses on the genome thereof by enhancement of the promoter activity of the enzyme gene or substitution with another promoter.

In the present invention, *Escherichia coli* means *Escherichia coli* that can be made to have the ability to produce isopropyl alcohol from a plant-derived raw material by using a certain means, regardless of whether or not the *Escherichia coli* originally has the ability to produce isopropyl alcohol from a plant-derived raw material.

Here, the *Escherichia coli* to which the respective genes are to be introduced may not have isopropyl alcohol production ability, and may be any *Escherichia coli* that allows the introduction or modification of the respective genes.

The *Escherichia coli* may more preferably be *Escherichia coli* to which isopropyl alcohol production ability has been imparted in advance. By using such *Escherichia coli*, isopropyl alcohol can more efficiently be produced. Especially, according to the present invention, sucrose assimilation ability can be imparted to *Escherichia coli* that does not have innate sucrose assimilation ability, whereby isopropyl alcohol can be efficiently produced from sucrose. Examples of the *Escherichia coli* that does not have innate sucrose assimilation ability include K12 strain, B strain, C strain, and strains derived therefrom.

An example of such isopropyl alcohol-producing *Escherichia coli* is an isopropyl alcohol-producing bacterium to which acetoacetate decarboxylase activity, isopropyl alcohol dehydrogenase activity, CoA transferase activity, and thiolase activity have been imparted so as to be capable of producing isopropyl alcohol from a plant-derived raw material, and which is described in WO 2009/008377 pamphlet.

A method for producing isopropyl alcohol according to the present invention includes producing isopropyl alcohol from a sucrose-containing plant-derived raw material by using the above-described isopropyl alcohol-producing *Escherichia coli*. More specifically, the method includes a process in which the above-described isopropyl alcohol-producing *Escherichia coli* is brought into contact with a sucrose-containing plant-derived raw material and cultured, and a collection process in which isopropyl alcohol generated as a result of the contact is collected.

The plant-derived raw material used in the above-described isopropyl alcohol production method may be, without particular limitation, any sucrose-containing plant-derived raw material that is a carbon source obtained from a plant. In the present invention, the plant-derived raw material refers to organs such as roots, stalks, stems, branches, leaves, flowers, and seeds, plant bodies including the plant organs, and decomposition products of the plant organs, and further encompasses carbon sources that can be used as carbon sources by microorganisms during cultivation from among carbon sources obtained from the plant bodies, the plant organs, or decomposition products thereof.

The carbon sources included in such plant-derived raw materials generally include, besides sucrose, sugars such as starch, glucose, fructose, xylose, and arabinose, or herbaceous and ligneous plant decomposition products or cellulose hydrolysates, each of which contains the above ingredients in large amounts, and combinations thereof. The carbon sources in the present invention may further include vegetable oil-derived glycerin or fatty acids.

Preferable examples of the plant-derived raw material in the present invention include agricultural products such as grain, corn, rice, wheat, soybean, sugarcane, beet, cotton, and the like, or combinations thereof. The form thereof as the raw material is not specifically limited, and may be a crude product, squeezed juice, a crushed product, or the like. Alternatively, the plant-derived raw material may be in a form that consists of the carbon source alone.

In the culture process, the contact between the isopropyl alcohol-producing *Escherichia coli* and a plant-derived raw material is generally made by culturing the isopropyl alcohol-producing *Escherichia coli* in a culture medium containing the plant-derived raw material.

The density of contact between the plant-derived raw material and the isopropyl alcohol-producing *Escherichia coli* may be varied depending on the activity of the isopropyl alcohol-producing *Escherichia coli*. In general, the concentration of the plant-derived raw material in the culture medium may be such that the initial sugar concentration in terms of glucose may be set to be 20% by mass or lower relative to the total mass of the mixture. From the viewpoint of sugar tolerance of *Escherichia coli*, the initial sugar concentration is preferably set to be 15% by mass or lower. Other components may be added in usual addition amounts for microorganism culture media, without particular limitation.

The content of the isopropyl alcohol-producing *Escherichia coli* in the culture medium may be varied with the kind and activity of *Escherichia coli*, and the amount of a preculture bacterial liquid to be added when starting cultivation may generally be set to be from 0.1 to 30% by mass relative to the culture liquid, and is preferably set to be from 1 to 10% by mass relative to the culture liquid from the viewpoint of controlling culture conditions.

The culture medium to be used for culture of the isopropyl alcohol-producing *Escherichia coli* may be any culture medium that includes a carbon source, a nitrogen source, inorganic ions, and organic trace elements, nucleic acids, vitamins and the like required by microorganisms to produce isopropyl alcohol, without particular limitation.

Besides sucrose, sugars such as glucose, fructose, and molasses, organic acids such as fumaric acid, citric acid and succinic acid, and alcohols such as methanol, ethanol and glycerol, and the like are used as carbon sources, as appropriate. Inorganic nitrogen sources such as organic ammonium salts, inorganic ammonium salts, ammonia gas, and aqueous ammonia, organic nitrogen sources such as protein hydrolysates, and the like are used as nitrogen sources, as appropriate. A magnesium ion, a phosphate ion, a potassium ion, an iron ion, a manganese ion, and the like are used as inorganic ions, as appropriate, in accordance with the necessity.

Vitamins, amino acids, and the like, and yeast extracts, peptone, corn steep liquor, casein decomposition products, and others, which contain vitamins and amino acids, are used as organic trace elements, as appropriate.

The culture medium may include other additive components, such as antibiotics, that are usually added to microorganism culture mediums, in usually-employed amounts. It is preferable to add an appropriate amount of anti-foaming agent in order to suppress foaming during reaction. The amounts of these components in the culture medium are not particularly limited as long as the amounts are within the ranges usually applied to cultivation of *Escherichia coli*.

The culture medium to be used in the present invention is preferably a liquid medium, in consideration of application to industrial production.

In the present method, isopropyl alcohol is preferably collected in the state of being dissolved in a mixture solution of the culture medium and the plant-derived raw material, or in the state of being dissolved in a trap solution, from the viewpoints of separation and collection ratio. The trap solution may be, for example, an organic solvent such as toluene or dimethyl formamide, or water. Among them, the trap solution is preferably water, with which volatile contaminants generated as by-products during production of isopropyl alcohol and isopropyl alcohol can easily be separated. Examples of the collection method include the method described in WO 2009/008377 pamphlet.

Figure 1:
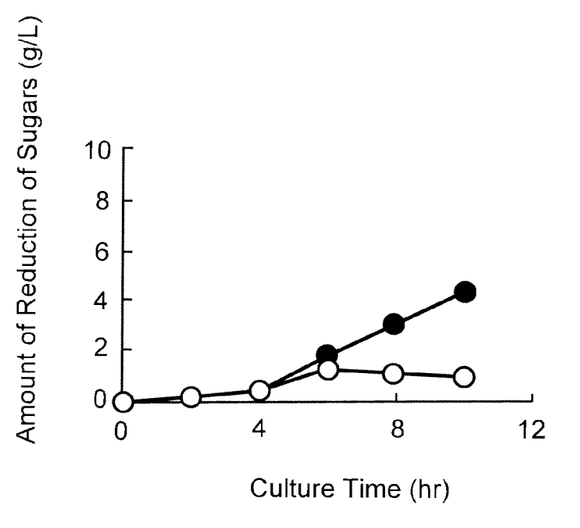
FIG. 1 is a graph showing the amount of reduction in sugars in the culture supernatant when an *Escherichia coli* B strain is cultured for 10 hours using glucose and fructose as sugar sources.

An example of apparatuses applicable to the isopropyl alcohol production method in which isopropyl alcohol can be collected in the state of being dissolved in the trap solution or the mixture is the production apparatus shown in FIG. 1 of WO 2009/008377 pamphlet.

In the production apparatus, an injection pipe for injecting a gas from outside the apparatus is connected to a culture tank that contains the culture medium including the isopropyl alcohol-producing bacterium and the plant-derived raw material, thereby enabling aeration to the culture medium.

A trap tank that contains a trap solution as the trap solution is connected to the culture tank via a connection pipe. A gas or liquid that has moved to the trap tank contacts the trap solution, and bubbling occurs.

As a result, isopropyl alcohol, which has been produced in the culture tank by cultivation under aeration, is evaporated due to aeration, and thus easily separated from the culture medium, and is trapped in the trap solution in the trap tank. As a result, isopropyl alcohol can be produced in a more purified state in a simple and continuous manner.

EXAMPLES

Hereinafter, examples of the present invention are described, but the invention is not limited thereto. In the description, "%" is based on mass unless otherwise specified.

Example 1

Construction of Expression Vector for Thiolase Gene Derived from *Escherichia Coli*, CoA Transferase Gene Derived from *Escherichia Coli*, Acetoacetate Decarboxylase Gene Derived from Bacterium of Genus *Clostridium*, Isopropyl Alcohol Dehydrogenase Gene Derived from Bacterium of Genus *Clostridium*, and Invertase Gene Derived from *Escherichia coli* O157, and Transformant with the Expression Vector The amino acid sequences of thiolase of *Escherichia coli* and CoA transferase of *Escherichia coli* and the base sequences of the genes thereof have already been reported. Specifically, the thiolase-encoding gene is described at 2324131 to 2325315 of the *Escherichia coli* MG1655 strain genome sequence registered with GenBank accession number U00096. In addition, the CoA transferase-encoding gene is described at 2321469 to 2322781 of the *Escherichia coli* MG1655 strain genome sequence mentioned above.

The promoter sequence of an *Escherichia coli*-derived glyceraldehyde 3-phosphate dehydrogenase (hereinafter sometimes referred to as GAPDH) that is described at 397 to 440 in the base sequence information of GenBank accession number X02662 may be used as the base sequence of a promoter necessary for expressing the genes.

In order to obtain the GAPDH promoter, amplification by a PCR method was carried out using the genomic DNA of *Escherichia coli* MG1655 strain as a template and using cgagctacatatgcaatgattgacacgattccg (SEQ ID NO: 1) and cgcgcgcatgctatttgttagtgaataaaagg (SEQ ID NO: 2). The resultant DNA fragment was digested with restriction enzymes NdeI and SphI, as a result of which a DNA fragment of about 100 bp corresponding to the GAPDH promoter was obtained. The obtained DNA fragment was mixed with a fragment obtained by digesting a plasmid pBR322 (GenBank accession number J01749) with restriction enzymes NdeI and SphI, and the mixed fragments were ligated using a ligase.

Thereafter, a competent cell of *Escherichia coli* DH5α strain (DNA-903: Toyobo Co., Ltd.) was transformed with the ligation product, and a transformant that grew on an LB agar plate containing 50 µg/mL ampicillin was obtained. The obtained colony was cultured overnight at 37° C. in an LB liquid medium containing 50 µg/mL ampicillin, a plasmid was recovered from the bacterial cells obtained, and it was confirmed that the GAPDH promoter was properly inserted. The plasmid was named pBRgapP.

In order to obtain the isopropyl alcohol dehydrogenase gene, amplification by a PCR method was carried out using the genomic DNA of *Clostridium beijerinckii* NRRL B-593 as a template and using aatatgcatgctggtggaacatatgaaaggttttgcaatgctagg (SEQ ID NO: 3) and gcggatccggtacct-tataatataactactgctttaattaagtc (SEQ ID NO: 4). The resultant DNA fragment was digested with restriction enzymes SphI and BamHI, as a result of which an isopropyl alcohol dehydrogenase fragment of about 1.1 kbp was obtained. The obtained DNA fragment was mixed with a fragment obtained by digesting the previously-prepared pBRgapP with restriction enzymes SphI and BamHI, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 µg/mL ampicillin was obtained. The obtained colonies were cultured overnight at 37° C. in an LB liquid medium containing 50 µg/mL ampicillin, a plasmid was recovered from the bacterial cells obtained, and it was confirmed that the isopropyl alcohol dehydrogenase was properly inserted. The plasmid was named pGAP-IPAdh.

In order to obtain the *Escherichia coli*-derived thiolase gene, amplification by a PCR method was carried out using the genomic DNA of *Escherichia coli* MG1655 strain as a template and using atggatccgctggtggaacatat-gaaaaattgtgtcatcgtcag (SEQ ID NO: 5) and gcagaagcttgtcta-gattaattcaaccgttcaatcaccatc (SEQ ID NO: 6). The resultant DNA fragment was digested with restriction enzymes BamHI and HindIII, as a result of which a thiolase fragment of about 1.2 kbp was obtained. The obtained DNA fragment was mixed with a fragment obtained by digesting the previously-prepared plasmid pGAP-IPAdh with restriction enzymes BamHI and HindIII, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 mg/mL ampicillin was obtained. The obtained colonies were cultured overnight at 37° C. in an LB liquid medium containing 50 µg/mL ampicillin, a plasmid was recovered from the bacterial cells obtained, and it was confirmed that the thiolase gene was properly inserted. The plasmid was named pGAP-IPAdh-atoB.

In order to obtain an *Escherichia coli*-derived CoA transferase α subunit gene, amplification by a PCR method was carried out using the genomic DNA of *Escherichia coli* MG1655 strain as a template and using gctctagagctggtggaa-catatgaaaacaaaattgatgacattacaagac (SEQ ID NO: 7) and tag-caagcttctactcgagttatttgctctcctgtgaaacg (SEQ ID NO: 8). The resultant DNA fragment was digested with restriction enzymes XbaI and HindIII, as a result of which a CoA transferase α subunit fragment of about 600 bp was obtained. The obtained DNA fragment was mixed with a fragment obtained by digesting the previously-prepared plasmid pGAP-IPAdh-atoB with restriction enzymes XbaI and HindIII, and the mixed fragments were ligated using a ligase. Thereafter, a competent cell of *Escherichia coli* DH5α strain (DNA-903:

Toyobo Co., Ltd.) was transformed with the ligation product, and a transformant that grew on an LB agar plate containing 50 μg/mL of ampicillin was obtained. The obtained colonies were cultured overnight at 37° C. in an LB liquid medium containing 50 μg/mL ampicillin, a plasmid was recovered from the bacterial cells obtained, and it was confirmed that the CoA transferase α subunit gene was properly inserted. The plasmid was named pGAP-IPAdh-atoB-atoD.

Further, in order to obtain an *Escherichia coli*-derived CoA transferase β subunit gene, amplification by a PCR method was carried out using the genomic DNA of *Escherichia coli* MG1655 strain as a template and using aagtctcgagctggtggaa-catatggatgcgaaacaacgtattg (SEQ ID NO: 9) and ggccaagct-tcataaatcaccccgttgc (SEQ ID NO: 10). The resultant DNA fragment was digested with restriction enzymes XhoI and HindIII, as a result of which a CoA transferase β subunit fragment of about 600 bp was obtained. The obtained DNA fragment was mixed with a fragment obtained by digesting the previously-prepared plasmid pGAP-IPAdh-atoB-atoD with restriction enzymes XhoI and HindIII, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 μg/mL ampicillin was obtained. The obtained colonies were cultured overnight at 37° C. in an LB liquid medium containing 50 μg/mL ampicillin, a plasmid was recovered from the bacterial cells obtained, and it was confirmed that the CoA transferase β subunit gene was properly inserted. The plasmid was named pGAP-IPAdh-atoB-atoD-atoA.

Furthermore, in order to obtain *Escherichia coli* O157 strain-derived cscA, amplification by a PCR method was carried out using the genomic DNA of *Escherichia coli* O157 strain as a template and using gctggtggaacatatgacgcaatctc-gattgcatg (SEQ ID NO: 11) and ttaacccagttgccagagtgc (SEQ ID NO: 12). The resultant DNA fragment was phosphorylated at its terminal using T4 polynucleotide kinase, as a result of which a cscA fragment of about 1470 bp was obtained. The obtained DNA fragment was mixed with a fragment obtained by digesting the previously-prepared pGAP-IPAdh-atoB-atoD-atoA with a restriction enzyme HindIII, followed by conversion to blunt terminals using T4 DNA polymerase, and dephosphorylation of the terminals with alkaline phosphatase. The mixed fragments were ligated using a ligase. A competent cell of *Escherichia coli* DH5α strain (DNA-903: Toyobo Co., Ltd.) was transformed with the ligation product, and a transformant that grew on an LB agar plate containing 50 μg/mL ampicillin was obtained. A plasmid was recovered from the bacterial cells obtained, and it was confirmed that the 3'-end side of the CoA transferase β subunit gene was ligated to the 5'-end side of cscA, and that cscA was properly inserted. The plasmid was named pGAP-IPAdh-atoB-atoD-atoA-cscA.

The genome of *Escherichia coli* O157 is available from the Institute for Reference Materials and Measurements.

In order to obtain an acetoacetate decarboxylase gene, amplification by a PCR method was carried out using the genomic DNA of *Clostridium acetobutylicum* ATCC824 as a template and using caggtaccgctggtggaacatatgt-taaaggatgaagtaattaaacaaattagc (SEQ ID NO: 13) and gcg-gatccttacttaagataatcatatataacttcagc (SEQ ID NO: 14). The resultant DNA fragment was digested with restriction enzymes KpnI and BamHI, as a result of which an acetoacetate decarboxylase fragment of about 700 bp was obtained. The obtained DNA fragment was mixed with a fragment obtained by digesting the previously-prepared plasmid pGAP-IPAdh-atoB-atoD-atoA-cscA with restriction enzymes KpnI and BamHI, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 μg/mL ampicillin. The obtained colonies were cultured overnight at 37° C. in an LB liquid medium containing 50 μg/mL ampicillin, a plasmid was recovered from the bacterial cells obtained, and it was confirmed that the acetoacetate decarboxylase gene was properly inserted. The plasmid was named pGAP-Iaaa-cscA. *Escherichia coli* B strain (ATCC11303) was transformed with the plasmid, and was cultured overnight at 37° C. in an LB agar plate containing 50 μg/mL ampicillin. The resultant transformant was named pGAP-Iaaa-cscA/B strain.

Example 2

Production of Isopropyl Alcohol from Sucrose by *Escherichia Coli* pGAP-Iaaa-cscA/B Strain Using 3 L Culture Tank In this example, isopropyl alcohol was produced using a production apparatus shown in FIG. 1 of the WO 2009/008377 pamphlet. The culture tank used was a tank having a capacity of 3 L and the trap tank used was a tank having a capacity of 10 L. The culture tank, the trap tank, the injection pipe, the connection pipe, and the discharge pipe were all made of glass. Into the trap tank, water as a trap solution (trap water) in an amount of 6 L was injected. The culture tank was equipped with a drain pipe, and the culture liquid increased by feeding of sugar and a neutralizer was discharged to outside the culture tank, as appropriate.

As preculture, the pGAP-Iaaa-cscA/B strain obtained in Example 1 was inoculated into an Erlenmeyer flask having a capacity of 100 mL and containing 25 mL of an LB Broth, Miller culture liquid (Difco 244620) containing 50 μg/mL ampicillin, and cultured overnight at a culture temperature of 35° C. while stirring at 120 rpm. The entire amount of the culture liquid was transferred into a culture tank having a capacity of 3 L (culture apparatus BMJ-01 manufactured by ABLE Co., Ltd.) and containing 1475 g of a culture medium having the following composition, and was cultivated.

The Cultivation was carried out at an aeration amount of 1.5 L/min, a stirring speed of 550 rpm, a culture temperature of 35° C., and pH of 7.0 (adjusted with a $NH_3$ solution) under atmospheric pressure. A 40 wt/wt % sucrose aqueous solution was added at a flow rate of 5 g/L/hour during the period from the initiation of the cultivation to 8 hours after the initiation of the cultivation, and, thereafter, the addition of the 40 wt/wt % sucrose aqueous solution was carried out at a flow rate of 15 g/L/hour. The bacterium culture liquid was sampled 48 hours after the initiation of the cultivation, and bacterial cells were removed by centrifugal operation. Thereafter, the amount of isopropyl alcohol accumulated in the resultant culture supernatant was measured by HPLC according to an ordinary method.

(Composition of Culture Medium)

Corn steep liquor (manufactured by Nihon Shokuhin Kako Co., Ltd.): 20 g/L $Fe_2SO_4.7H_2O$: 0.09 g/L $K_2HPO_4$: 2 g/L $KH_2PO_4$: 2 g/L $MgSO_4.7H_2O$: 2 g/L (NH$_4$)$_2$SO$_4$: 2 g/L
ADECANOL LG126 (Adeka Corporation): 0.6 g/L
(The rest: water)

As a result, at 48 hours after the initiation of the cultivation, accumulation of 5.9 g/L of isopropyl alcohol was confirmed. The measured value is a sum of the amounts in the culture liquid and the trap water (6 L) after the cultivation.

The results demonstrated that the introduction of cscA from among the sucrose non-PTS gene group resulted in decomposition of sucrose, and glucose and fructose, which are decomposition products, were quickly incorporated into the cells, and converted to isopropyl alcohol.

Example 3

Production of isopropyl alcohol from sucrose was tested in a case in which the expressions of CoA transferase genes (atoD and atoA) and a thiolase gene (atoB) on the genome of the host *Escherichia coli* were enhanced while the DNA size of the entire plasmid length was reduced by ligating only an acetoacetate decarboxylase gene, an isopropyl alcohol dehydrogenase gene, and cscA to the plasmid vector to be introduced.

Replacement of atoD Promoter on *Escherichia Coli* B Strain Genome by GAPDH Promoter The entire base sequence of the genomic DNA of *Escherichia coli* MG1655 strain is known (GenBank accession number U00096), and the base sequence of a gene (hereinafter sometimes abbreviated to atoD) that encodes a CoA transferase α subunit of *Escherichia coli* MG1655 strain has also been reported. Specifically, atoD is described at 2321469 to 2322131 of the *Escherichia coli* MG1655 strain genome sequence registered with GenBank accession number U00096.

The promoter sequence of an *Escherichia coli*-derived glyceraldehyde 3-phosphate dehydrogenase (hereinafter sometimes referred to as GAPDH) that is described at 397 to 440 in the base sequence information of GenBank accession number X02662 may be used as the base sequence of a promoter necessary for expressing the genes. In order to obtain the GAPDH promoter, amplification by a PCR method was carried out using the genomic DNA of *Escherichia coli* MG1655 strain as a template and using cgctcaattgcaatgattga-cacgattccg (SEQ ID NO: 15) and acagaattcgctatttgttagt-gaataaaagg (SEQ ID NO: 16). The resultant DNA fragment was digested with restriction enzymes MfeI and EcoRI, as a result of which a DNA fragment of about 100 bp encoding a GAPDH promoter was obtained. The obtained DNA fragment was mixed with a fragment obtained by digesting a plasmid pUC19 (GenBank accession number X02514) with restriction enzyme EcoRI followed by alkaline phosphatase treatment, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 µg/mL ampicillin was obtained. Ten of the obtained colonies were individually cultured at 37° C. overnight in an LB liquid medium containing 50 µg/mL ampicillin, plasmids were recovered, and plasmids from which the GAPDH promoter was not cut out when digested with restriction enzymes EcoRI and KpnI were selected. Further, the DNA sequences thereof were checked, and a plasmid in which the GAPDH promoter was properly inserted was named pUCgapP. The pUCgapP obtained was digested with restriction enzymes EcoRI and KpnI.

Furthermore, in order to obtain atoD, amplification by a PCR method was carried out using the genomic DNA of *Escherichia coli* MG1655 strain as a template and using cgaattcgctggtggaacatatgaaaacaaaattgatgacattacaagac (SEQ ID NO: 17) and gcggtaccttatttgctctcctgtgaaacg (SEQ ID NO: 18). The resultant DNA fragment was digested with restriction enzymes EcoRI and KpnI, as a result of which an atoD fragment of about 690 bp was obtained. The DNA fragment was mixed with the pUCgapP, which had previously been digested with restriction enzymes EcoRI and KpnI, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 µg/mL ampicillin was obtained. A plasmid was recovered from the bacterial cells obtained, and it was confirmed that atoD was properly inserted. The plasmid obtained was named pGAPatoD.

The *Escherichia coli* MG1655 strain is available from the American Type Culture Collection.

As described above, the base sequence of atoD in the genomic DNA of *Escherichia coli* MG1655 strain has also been reported. PCR was carried out using the genomic DNA of *Escherichia coli* MG1655 strain as a template, and using gctctagatgctgaaatccactagtcttgtc (SEQ ID NO: 19) and tactg-cagcgttccagcaccttatcaacc (SEQ ID NO: 20) prepared based on the gene information of a near-5' region of atoD of *Escherichia coli* MG1655 strain, as a result of which a DNA fragment of about 1.1 kbp was amplified.

In addition, PCR was carried out using the previously-prepared expression vector pGAPatoD as a template and using ggtctagagcaatgattgacacgattccg (SEQ ID NO: 21) prepared based on the sequence information of the GAPDH promoter of *Escherichia coli* MG1655 strain and the primer of SEQ ID NO: 18 prepared based on the sequence information of atoD of *Escherichia coli* MG1655 strain, as a result of which a DNA fragment of about 790 bp having the GAPDH promoter and atoD was obtained.

The fragments obtained above were digested with restriction enzymes PstI and XbaI, and XbaI and KpnI, respectively. The digested fragments were mixed with a fragment obtained by digesting a temperature-sensitive plasmid pTH18cs1 (GenBank accession number AB019610) [Hahimoto-Gotoh, T., Gene, 241, 185-191 (2000)] with PstI and KpnI, and the mixed fragments were ligated using a ligase. DH5α strain was transformed with the ligation product, and a transformant that grew at 30° C. on an LB agar plate containing 10 µg/ml chloramphenicol was obtained. The obtained colony was cultured overnight at 30° C. in an LB agar plate containing 10 µg/ml chloramphenicol, and a plasmid was recovered from the bacterial cells obtained. *Escherichia coli* B strain (ATCC11303) was transformed with the obtained plasmid, and was cultured overnight at 30° C. in an LB agar plate containing 10 µg/ml chloramphenicol, and a transformant was obtained. The obtained transformant was inoculated into an LB agar plate containing 10 µg/ml of chloramphenicol, and cultured overnight at 30° C. The cultured bacterial cells obtained were applied onto an LB agar plate containing 10 µg/ml chloramphenicol, and were cultured at 42° C., and colonies were obtained. The obtained colonies were cultured at 30° C. for 2 hours in an LB liquid medium not containing an antibiotic, and applied onto an LB agar plate not containing an antibiotic, as a result of which colonies that grow at 42° C. were obtained.

From the resultant colonies, 100 colonies were randomly picked up, each of which was then grown in an LB agar plate free of antibiotic and an LB agar plate containing 10 µg/ml chloramphenicol. Chloramphenicol-sensitive clones were selected, and, from the chromosomal DNAs of the selected clones, a fragment of about 790 bp including the GAPDH promoter and atoD was amplified by PCR, and a strain in which an atoD promoter region was replaced by the GAPDH promoter was selected. Then, a clone satisfying the above conditions was named an *Escherichia coli* B strain atoD-deleted GAPp-atoD genome-inserted strain.

The *Escherichia coli* B strain (ATCC11303) is available from the American Type Culture Collection, which is a bank of cells, microorganisms, and genes.

Example 4

Construction of Expression Vector for Acetoacetate Decarboxylase Gene Derived from Bacterium of Genus *Clostridium* and Isopropyl Alcohol Dehydrogenase Gene Derived from Bacterium of Genus *Clostridium*, and Transformant with the Expression Vector An acetoacetate decarboxylase of a bacterium of the genus *Clostridium* is described at GenBank accession number M55392 and an isopropyl alcohol dehydrogenase thereof is described at GenBank accession number AF157307.

In order to obtain the isopropyl alcohol dehydrogenase gene, amplification by a PCR method was carried out using the genomic DNA of *Clostridium beijerinckii* NRRL B-593 as a template and using AATATGCATGCTGGTGGAA-CATATGAAAGGTTTTGCAATGCTAGG (SEQ ID NO: 3) and gcggatccttataatataactactgctttaattaagtc (SEQ ID NO: 22). The resultant DNA fragment was digested with restriction enzymes SphI and BamHI, as a result of which an isopropyl alcohol dehydrogenase fragment of about 1.1 kbp was obtained. The obtained DNA fragment was mixed with a fragment obtained by digesting the previously-prepared plasmid pBRgapP with restriction enzymes SphI and BamHI, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 μg/mL ampicillin was obtained. The obtained colony was cultured at 37° C. overnight in an LB liquid medium containing 50 μg/mL ampicillin, and a plasmid was recovered from the bacterial cells obtained, and it was confirmed that the IPAdh was properly inserted. The plasmid was named pGAP-IPAdh.

In order to obtain the acetoacetate decarboxylase gene, amplification by a PCR method was carried out using the genomic DNA of *Clostridium acetobutylicum* ATCC824 as a template and using caggatccgctggtggaacatatgt-taaaggatgaagtaattaaacaaattagc (SEQ ID NO: 23) and ggaat-tcggtaccttacttaagataatcatatataacttcagc (SEQ ID NO: 24). The resultant DNA fragment was digested with restriction enzymes BamHI and EcoRI, as a result of which an acetoacetate decarboxylase fragment of about 700 bp was obtained. The obtained DNA fragment was mixed with a fragment obtained by digesting the previously-prepared plasmid pGAP-IPAdh with restriction enzymes BamHI and EcoRI, and the mixed fragments were ligated using a ligase. A competent cell of *Escherichia coli* DH5α strain (DNA-903: Toyobo Co., Ltd.) was transformed with the ligation product, and a transformant that grew on an LB agar plate containing 50 μg/mL ampicillin was obtained. The colony obtained was cultured at 37° C. overnight in an LB liquid medium containing 50 μg/mL ampicillin. A plasmid was recovered from the bacterial cells obtained, and it was confirmed that adc was properly inserted. The plasmid was named pGAP-Ia.

A competent cell of the *Escherichia coli* B strain atoD-deleted GAPp-atoD genome-inserted strain prepared in Example 3 was transformed with the plasmid pGAP-Ia, and was cultured at 37° C. overnight in an LB agar plate containing 50 μg/mL ampicillin, as a result of which an *Escherichia coli* pGAP-Ia/GAPp-atoD genome-inserted strain was obtained.

The *Clostridium acetobutylicum* ATCC824 and the *Escherichia coli* B strain are available from the American Type Culture Collection, which is a bank of cells, microorganisms, and genes. The *Clostridium beijerinckii* NRRL B-593 is available from the VTT Culture Collection, which is a bank of cells and microorganisms.

Example 5

Construction of Expression Vector Acetoacetate Decarboxylase Gene Derived from Bacterium of Genus *Clostridium*, Isopropyl Alcohol Dehydrogenase Gene Derived from Bacterium of Genus *Clostridium*, and Invertase Gene Derived from *Escherichia Coli* O157, and Transformant with the Expression Vector The entire base sequence of the genomic DNA of *Escherichia coli* O157 strain is known (GenBank accession number AE005174), and the base sequence of a gene (hereinafter sometimes abbreviated to cscA) that encodes the invertase of the *Escherichia coli* O157 strain has also been reported. Specifically, cscA is described at 3274383 to 3275816 of the *Escherichia coli* O157 strain genome sequence registered with GenBank accession number AE005174.

In order to obtain cscA, amplification by a PCR method was carried out using the genomic DNA of *Escherichia coli* O157 strain as a template and using ATGGTACCGCTG-GTGGAACATATGACGCAATCTCGATTGCATG (SEQ ID NO: 25) and CGAATTCTTAACCCAGTTGCCA-GAGTGC (SEQ ID NO: 26). The resultant DNA fragment was digested with restriction enzymes KpnI and EcoRI, as a result of which a cscA fragment of about 1470 bp was obtained. The DNA fragment was mixed with a fragment obtained by digesting the pGAP-Ia, which had previously been prepared in Example 4 (the expression vector for the acetoacetate decarboxylase gene derived from the bacterium of the genus *Clostridium* and the isopropyl alcohol dehydrogenase gene derived from the bacterium of the genus *Clostridium*), with restriction enzymes KpnI and EcoRI, and the mixed fragments were ligated using a ligase. Thereafter, a competent cell of *Escherichia coli* DH5α strain (DNA-903: Toyobo Co., Ltd.) was transformed with the ligation product, and a transformant that grew on an LB agar plate containing 50 μg/mL ampicillin was obtained. A plasmid was recovered from the bacterial cells obtained, and it was confirmed that cscA was properly inserted. This plasmid was named pGAP-Ia-cscA.

A competent cell of the *Escherichia coli* B strain atoD-deleted GAPp-atoD genome-inserted strain prepared in Example 3 was transformed with the plasmid pGAP-Ia-cscA, and was cultured at 37° C. overnight in an LB agar plate containing 50 μg/mL ampicillin, as a result of which an *Escherichia coli* pGAP-Ia-cscA/GAPp-atoD genome-inserted strain was obtained.

The *Escherichia coli* O157 genome is available from the Institute for Reference Materials and Measurements.

Example 6

Production of Isopropyl Alcohol from Sucrose by *Escherichia Coli* pGAP-Ia-cscA/GAPp-atoD Genome-Inserted Strain Using 3 L Culture Tank Using the *Escherichia Coli* pGAP-Ia-cscA/GAPp-atoD genome-inserted strain obtained in Example 5, the production of isopropyl alcohol was examined in the same manner as in Example 2.

In addition, the amounts of sucrose, glucose, and fructose accumulated in the culture tank were measured, and the results are shown in Table 1.

As a result, at 48 hours after the initiation of the cultivation, accumulation of 31.4 g/L of isopropyl alcohol was observed. Each of the measured values is a sum of the amounts in the culture liquid and the trap water after the cultivation.

TABLE 1

| Time hr | Added amount of 40% Sucrose g | Residual sugar | | | Accumulation amount of isopropyl alcohol g/L |
| --- | --- | --- | --- | --- | --- |
| | | Sucrose g/L | Glucose g/L | Fructose g/L | |
| 0 | 0.0 | 0.00 | 0.00 | 0.00 | 0.00 |
| 3 | 23.6 | 22.07 | 0.00 | 0.00 | 0.00 |
| 6 | 67.2 | 46.05 | 0.02 | 0.03 | 0.43 |
| 10 | 152.1 | 78.28 | 0.76 | 0.00 | 6.43 |
| 24 | 384.6 | 0.00 | 0.00 | 0.00 | 11.87 |
| 30 | 536.0 | 0.00 | 0.00 | 0.00 | 18.28 |
| 48 | 1011.9 | 0.00 | 0.00 | 0.00 | 31.38 |

The results demonstrated that, when genes derived from a bacterium/bacteria of the genus *Clostridium* were selected for acetoacetate decarboxylase activity and isopropyl alcohol dehydrogenase activity, and these genes are introduced with only cscA from among the sucrose non-PTS gene group, sucrose was decomposed, and glucose and fructose as decomposition products were quickly incorporated into the cells, and converted to isopropyl alcohol. Further, in the results, although glucose and fructose must have been produced in equimolar amounts by the decomposition of sucrose, fructose did not accumulate in the culture medium, and it was observed that isopropyl alcohol was efficiently produced without being affected by catabolite repression by glucose.

Example 7

Production of Isopropyl Alcohol from Molasses by *Escherichia Coli* pGAP-Ia-cscA/GAPp-atoD Genome-Inserted Strain Using 1 L Culture Tank Production of isopropyl alcohol was tested in the same manner as in Example 6, except for using 80 wt/wt % molasses (manufactured by Dai-Nippon Meiji Sugar Co., Ltd.) in place of the 40 wt/wt % sucrose aqueous solution. At 48 hours after the initiation of the cultivation, accumulation of 29.4 g/L of isopropyl alcohol was observed. The measured value is a sum of the amounts in the culture liquid and the trap water after the cultivation.

Comparative Example 1

Production of Isopropyl Alcohol by *Escherichia Coli* pGAP-Ia/GAPp-atoD Genome-Inserted Strain Using 3-L Culture Tank Cultivation with isopropyl alcohol was tested with respect to the pGAP-Ia/GAPp-atoD genome-inserted strain prepared in Example 4, under the same conditions as in Example 2. As a result, the production of isopropyl alcohol was not confirmed even after 48 hours, and the added sucrose remained in the culture supernatant in almost the same amount.

This demonstrates that isopropyl alcohol cannot be produced without introduction of CscA even when isopropyl alcohol production ability has been imparted.

Comparative Example 2

Production of Isopropyl Alcohol by *Escherichia Coli* pGAP-Ia-cscA/B Strain Using 3 L Culture Tank

*Escherichia coli* B strain (ATCC 11303) was transformed with the plasmid pGAP-Ia-cscA prepared in Example 5, and was cultured at 37° C. overnight in an LB agar plate containing 50 μg/mL ampicillin. The resultant transformant was named pGAP-Ia-cscA/B strain. Cultivation with isopropyl alcohol was tested with respect to the prepared pGAP-Ia-cscA/B strain, under the same conditions as in Example 2. At 48 hours, production of isopropyl alcohol was not observed.

This demonstrates that isopropyl alcohol cannot be produced unless isopropyl alcohol production ability is imparted, even when CscA alone is introduced into the *Escherichia coli* B strain.

Comparative Example 3

Confirmation of Catabolite Repression by Glucose in *Escherichia Coli* B Strain

The B strain, which is the host of an isopropyl alcohol-producing *Escherichia coli* according to the present invention, was confirmed to be *Escherichia coli* that is intrinsically influenced by catabolite repression by glucose.

As preculture, *Escherichia coli* B strain (ATCC11303) was inoculated in a plastic tube having a capacity of 14 mL (2057 manufactured by FALCON Co., Ltd.) and containing 5 mL of LB Broth, Miller culture liquid (Difco 244620), and was cultivated at a culture temperature of 37° C. while stirring at 120 rpm. Then, 0.3 mL of the preculture liquid was transferred into each of baffled flasks having a capacity of 100 mL and containing 30 mL of culture media of the compositions of 1 to 4 shown in Table 2, respectively, and cultivated. The cultivation was carried out at a stirring speed of 120 rpm and a culture temperature of 37° C.

At 0, 2, 4, 6, 8, and 10 hours after the initiation of the cultivation, the culture liquids of the bacterial cells were sampled, from which the bacterial cells were removed by centrifugal operation. Then, the contents of glucose and fructose in the resultant culture supernatant were measured by a F-kit glucose/fructose (product number: 139106 manufactured by J.K. International Co., Ltd). FIG. 1 shows the results. In FIG. 1, the black circles represent the amounts of reduction of glucose and the white circles represent the amounts of reduction of fructose, respectively. Furthermore, the degree of reduction of glucose or fructose was calculated for each culture time starting from 0 hour of cultivation. Table 2 shows the amounts of reduction of glucose in the respective media after 10 hours.

TABLE 2

|  |  | No. | | | |
| --- | --- | --- | --- | --- | --- |
|  |  | 1 | 2 | 3 | 4 |
| M9 culture medium | NH$_2$Cl$_4$ (g/L) | 10 | 10 | 10 | 10 |
|  | Na$_2$HPO$_4$—12H$_2$O (g/L) | 17.1 | 17.1 | 17.1 | 17.1 |
|  | KH$_2$PO$_4$ (g/L) | 3 | 3 | 3 | 3 |
|  | NaCl (g/L) | 0.5 | 0.5 | 0.5 | 0.5 |
|  | MgSO$_4$—7H$_2$O (mg/L) | 490 | 490 | 490 | 490 |
|  | CaCl$_2$—2H$_2$O (mg/L) | 14.7 | 14.7 | 14.7 | 14.7 |
|  | FeSO$_4$—7H$_2$O (mg/L) | 2.8 | 2.8 | 2.8 | 2.8 |
|  | Thiamine-HCl (mg/L) | 10 | 10 | 10 | 10 |
| Sugars | glucose (g/L) | 0 | 9 | 18 | 0 |
|  | fructose (g/L) | 0 | 9 | 0 | 18 |
|  | (The rest: water) | | | | |
| Amount of Reduction of glucose (g/L) | | — | 4.4 | 5.1 | — |
| Amount of Reduction of fructose (g/L) | | — | 1.0 | — | 3.4 |

As shown in Table 2, when comparing the amounts of reduction of fructose and glucose after 10 hours, the value is 3.4 g/L in the case of culture medium No. 4 of which the sugar source includes only fructose, whereas the uptake of fructose is suppressed in the case of culture medium No. 2 of which the sugar source includes both glucose and fructose. This confirmed that, when the sugar source is fructose alone, the B strain incorporates fructose similarly to incorporation of glucose, whereas the incorporation of fructose in the B strain is suppressed when glucose and fructose coexist.

Thus, according to the present invention, there can be provided an isopropyl alcohol-producing *Escherichia coli* and a method for producing isopropyl alcohol that are useful for efficient production of isopropyl alcohol from sucrose, which is inexpensive and has high industrial utility value.

The disclosure of Japanese Patent Application No. 2009-214694, filed Sep. 16, 2009, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. An isolated isopropyl alcohol-producing *Escherichia coli* comprising a heterologous sucrose hydrolase gene that belongs to a sucrose non-PTS genes group, and an imparted or enhanced isopropyl alcohol production system,
   wherein no other genes from the sucrose non-PTS genes group are incorporated into the *E. Coli* besides the sucrose hydrolase gene.

2. The isolated isopropyl alcohol-producing *Escherichia coli* according to claim 1, wherein the isopropyl alcohol-producing *Escherichia coli* is an *Escherichia coli* to which an acetoacetate decarboxylase activity, an isopropyl alcohol dehydrogenase activity, a CoA transferase activity, and a thiolase activity have been imparted.

3. The isolated isopropyl alcohol-producing *Escherichia coli* according to claim 2, wherein the acetoacetate decarboxylase activity, the isopropyl alcohol dehydrogenase activity, the CoA transferase activity, and the thiolase activity are obtained by introduction of genes encoding respective enzymes which are derived from at least one selected from the group consisting of bacteria of the genus *Clostridium*, bacteria of the genus *Bacillus*, and bacteria of the genus *Escherichia*.

4. The isolated isopropyl alcohol-producing *Escherichia coli* according to claim 2, wherein the acetoacetate decarboxylase activity and the isopropyl alcohol dehydrogenase activity are obtained by introduction of genes encoding respective enzymes which are derived from at least one bacterium of the genus *Clostridium*, and the CoA transferase activity and the thiolase activity are obtained by introduction of genes encoding respective enzymes which are isolated from at least one bacterium of the genus *Escherichia*.

5. The isolated isopropyl alcohol-producing *Escherichia coli* according to claim 2, wherein the acetoacetate decarboxylase activity is obtained by introduction of a gene encoding an enzyme derived from *Clostridium acetobutylicum*, the isopropyl alcohol dehydrogenase activity is obtained by introduction of a gene encoding an enzyme derived from *Clostridium beijerinckii*, and the CoA transferase activity and the thiolase activity are obtained by introduction of genes encoding respective enzymes isolated from *Escherichia coli*.

6. The isolated isopropyl alcohol-producing *Escherichia coli* according to claim 2, wherein a gene encoding the acetoacetate decarboxylase, a gene encoding the isopropyl alcohol dehydrogenase, and the gene encoding the sucrose hydrolase have been introduced using at least one plasmid, and the CoA transferase activity and the thiolase activity are obtained from genomic genes in the host *Escherichia coli*.

7. The isolated isopropyl alcohol-producing *Escherichia coli* according to claim 6, wherein a promoter for expressing a gene encoding the CoA transferase and a gene encoding the thiolase is at least one of a glyceraldehyde-3-phosphate dehydrogenase promoter or a serine hydroxymethyltransferase promoter.

8. The isolated isopropyl alcohol-producing *Escherichia coli* according to claim 2, wherein the acetoacetate decarboxylase activity, the isopropyl alcohol dehydrogenase activity, the CoA transferase activity and the thiolase activity are all obtained by introduction of genes encoding respective enzymes derived from at least one bacterium of the genus *Clostridium*.

9. A method for producing isopropyl alcohol, comprising producing isopropyl alcohol from a sucrose-containing plant-derived raw material using the isolated isopropyl alcohol-producing *Escherichia coli* according to claim 1.

* * * * *